United States Patent [19]
Endres et al.

[11] 3,931,329
[45] Jan. 6, 1976

[54] ALDEHYDE CONDENSATION PRODUCTS OF FLUOROALIPHATIC PHENOLS

[75] Inventors: Leland S. Endres, San Luis Obispo, Calif.; Leo F. Gehlhoff, Lake Elmo; Dallas D. Zimmerman, Shoreview, both of Minn.

[73] Assignee: Minnesota Mining and Manufacturing Company, St. Paul, Minn.

[22] Filed: Jan. 23, 1974

[21] Appl. No.: 435,669

Related U.S. Application Data

[62] Division of Ser. No. 85,278, Oct. 29, 1970, Pat. No. 3,832,409.

[52] U.S. Cl. .............................. 260/592; 260/558
[51] Int. Cl.² ......................................... C07C 49/80
[58] Field of Search ........................... 260/592, 558

[56] References Cited
UNITED STATES PATENTS
3,832,409  8/1974  Endres et al. ................... 260/592

*Primary Examiner*—James O. Thomas, Jr.
*Assistant Examiner*—James H. Reamer
*Attorney, Agent, or Firm*—Alexander, Sell, Steldt & DeLaHunt

[57] ABSTRACT

Condensation products of aldehydes and fluoraliphatic phenols are substantive to wool, synthetic polyamides, leather and skin, the compositions preferably being extended with a suitable pharmaceutical medium. The condensation products are useful for the preparation of compositions that render such materials oil and water repellent.

4 Claims, No Drawings

ALDEHYDE CONDENSATION PRODUCTS OF FLUOROALIPHATIC PHENOLS

This is a division of application Ser. No. 85,278 filed Oct. 29, 1970, now U.S. Pat. No. 3,832,409.

BACKGROUND OF THE INVENTION

The present invention relates to improved compositions and methods that render the skin repellent to oil and water and more particularly to certain novel compositions adapted to topical application to provide the skin with protection which is not readily removed by mild abrasion or hot detergent solutions.

It has long been known that the skin can be protected by the application of lotions, creams, and various other emollient compositions. These preparations are intended to exert a beautifying, softening and lubricating effect on the skin and may even contain medicinal ingredients. Other compositions have been described which will prevent absorption of harmful or cosmetically undesirable substances. However, the preparations heretofore known for the purpose described, while effective to some degree, have all suffered from certain disadvantages. Mere emollients fail to protect the skin from exposure to injurious materials and only serve as palliative remedies afterwards. Barrier creams have been useful for certain specific conditions, but heretofore have failed to have broad general applicability. Furthermore, in maintaining personal hygiene, for example, by washing the hands, these compositions of the prior art are largely removed and repeated applications of the compositions are necessary. Obviously, the benefits obtained from these applications are not lasting since the protection is readily removed.

To provide skin protective compositions that resist removal from the skin by washing, particular ingredients have been incorporated into various compositions. For example, U.S. Pat. No. 2,727,846 teaches the incorporation of siloxanes into skin protective compositions. Such compositions, however, are easily transferred from the hands by touch or slight abrasion with other materials. This is a serious drawback in that even traces of such substances may bring about contamination of any surface touched. It is well known that the presence of even traces of silicones interfere with the action of adhesives, paints, and protective coatings. Furthermore, to be effective on the skin, a coating of a siloxane must be applied which is virtually continuous. Such a coating adversely impairs access of air and transpiration of moisture which is needed for the well-being of the skin.

To overcome the disadvantages of siloxane-containing skin protective compositions, it is proposed in U.S. Pat. No. 3,100,180 that the siloxane be replaced by a minor amount of a fluorocarbon elastomer. In U.S. Pat. No. 3,470,292, it is proposed that the disadvantage of siloxane in skin protective compositions be overcome by incorporating a phosphatide such as lecithin, kephalin, and sphingomyelin. At present there is no known effective composition which adequately protects the skin from water and oil known to applicants.

SUMMARY OF THE INVENTION

According to the present invention, there is provided a method for protecting the skin against injurious and undesirable materials such as hydrous and oily materials. More particularly, there is provided compositions for the prevention of "dish-pan hands" that is caused by repeated immersion of the hands in hot water containing soap or detergents. Still more particularly, skin protective compositions are provided which are substantive to human and animal skin and that, by reason of this substantivity, afford long lasting protection of the skin to water and oil. The skin protection compositions of the present invention are adapted to topical application, are resistant to abrasion, and may include medicaments.

In accordance with the present invention, the skin is made both oleophobic and also resistant to aqueous materials, including acids and bases and also protected from irritating and otherwise undesirable substances, by applying thereto compositions comprising certain aldehyde condensation products of certain fluoroaliphatic phenols in suitable pharmaceutical media as hereinafter defined. The compositions of the invention provide a long-lasting, indiscernible coating on the skin which is substantively bound to the skin and is not readily washed or abraded from the skin as are other topical protective preparations described heretofore. Although extremely effective in its protective action, the coating apparently does not affect the transpiration of the skin. The term, "substantive" as used herein, means that the material has a high degree of tenacity for the skin and is essentially nonremovable by normal procedures. It is believed, though applicants do not intend to be bound thereby, that the compositions of the present invention are actually chemically bound to the skin at least to some extent.

Broadly speaking, compositions useful for the purpose of the invention are provided by incorporating a minor amount of aldehyde condensation product of a fluoroaliphatic phenol into a major amount of an aqueous pharmaceutically acceptable extending medium of the aqueous emulsion type which may also contain a thixotropic bodying agent or thickening agent. Preferably there is employed from about 0.3 to about 20 percent by weight of the condensation product. The term "pharmaceutical extending medium" as used herein includes such preparations as the bases for lotions, creams, ointments, and the like water-based preparations for topical applications, which are sufficiently bodied so that the resultant composition is not watery or thin, but without limiting the viscosity or composition solely to a single type of preparation. For the purpose of the invention, the viscosity of the products described and claimed herein is required to be less than 1,000 centipoises when stirred at about 60 r.p.m. and may range upwardly to 1,000–5,000 centipoises, when determined using a Brookfield viscometer at about 25° C. The physical appearance of such preparations for topical application may range from that of a lotion through that of a flowable jelly, i.e., fairly stiff but flowable under mechanical force.

The aldehyde condensation products of certain fluoroaliphatic phenols that are disclosed herein are the significant and critical ingredient of the compositions of this invention. These condensation products are formed by the catalyzed reaction of an aldehyde with certain fluoroaliphatic phenols. The substantivity of these condensation products to human and animal skin and to other proteinaceous surfaces is believed to be obtained by reason of the phenolic hydroxyl group present in the condensation product. The oil and water repellent character is obtained by reason of the fluoroaliphatic group. Compounds possessing fluoroaliphatic groups have the greatest amount of substantivity if they possess at least two phenolic hydroxyl groups on separate aromatic rings. Aromatic compounds containing a fluoroaliphatic group and one or two hydroxyl groups on the same aromatic ring do not possess sufficient substantivity to provide detergent resistance to the compound.

The aldehyde condensation products of fluoroaliphatic phenols that are preferred for the compositions of this invention are the acid catalyzed reaction products of the aldehyde and certain fluoroaliphatic phenols.

For purposes of this invention, an aldehyde is an organic compound having the formula

RCHO wherein R is hydrogen or an organic radical having not more than seven carbon atoms, and which may be substituted by methyl, methoxy, ethyl, or ethoxy groups. More preferably, R is a lower alkyl group of the class $C_nH_{2n+1}$, where n is an integer of from 1 to 4. The aldehyde may be introduced into the reaction mixture either as a monomeric material or as the equivalent polymeric material which is convertible under condensation conditions to monomeric aldehyde. Suitable aldehydes (and materials capable of forming aldehydes) include
  acetaldehyde
  benzaldehyde
  butyraldehyde
  furfuraldehyde
  glutaraldehyde
  glyoxal
  paraformaldehyde
  paraldehyde
  propionaldehyde
  tetrahydrofurfuraldehyde
  trioxane
  isobutyraldehyde
The preferred aldehyde is formaldehyde.

For purposes of this invention, a fluoroaliphatic phenol is a compound that may be represented by the general formula $(H)_l A(OH)_m[(Q)_t(R_f)_p]_r$ in which $l$, $m$, $p$, and $r$ are each integers of 1 or 2; t is 0 or 1; H is hydrogen atom that is sufficiently reactive to undergo a catalyzed condensation reaction with an aldehyde; A is an aryl nucleus of about 6 to 15 carbon atoms; OH is a phenolic hydroxyl group; $R_f$ is a monovalent fluorinated saturated non-aromatic aliphatic radical and Q is a divalent group linking A to $R_f$.

Examples of A include aromatic nuclei such as benzene, naphthalene, diphenyl and diphenylmethane and their alkyl, aryl, alkoxy, aryloxy, and halo derivatives.

Examples of Q include the following and combinations thereof:
  alkylene —$(C_nH_{2n})$—
  alkenylene —$(C_nH_{2n-2})$—
  haloalkylene —$(C_nH_{2n-1}Cl)$—
  sulfonate —$OSO_2$—
  sulfonamide —$NR$—$SO_2$—
  carbonyl —$CO$—
  carbonamide —$NR$—$CO$—
  oxaalkylene —$C_nH_{2n}OC_nH_{2n}$—

In the above examples n is an integer from 1 to 15 and designates the number of carbon atoms in the alkylene or haloalkylene radical joining the $R_f$ group to the aryl group.

The fluoroaliphatic radical ($R_f$) is a monovalent fluorinated saturated non-aromatic aliphatic radical having at least 3 carbon atoms in the skeletal chain. This chain may be straight, branched or cyclic, and may be interrupted by divalent oxygen atoms or trivalent nitrogen atoms bonded only to carbon atoms. Preferably the chain does not contain more than one nitrogen atom or one oxygen atom for every two carbon atoms in the skeletal chain. A perfluoroalkyl radical is preferred, but an occasional hydrogen or chlorine atom may be present as substituents in the fluorinated aliphatic radical provided that not more than one such non-fluorine substituent is present in such radical for every two carbon atoms, and that such radical contains a terminal perfluoroalkyl group. "Terminal" in this connection refers to the position in the skeletal chain of the radical which is furthest removed from the group. Preferably, such a radical contains not more than a total of 20 carbon atoms whether r is 1 or 2 since such a large radical results in inefficient use of the fluorine content.

Examples of fluoroaliphatic phenols suitable for the preparation of the aldehyde condensation products of the present invention are shown in Table I below.

TABLE I

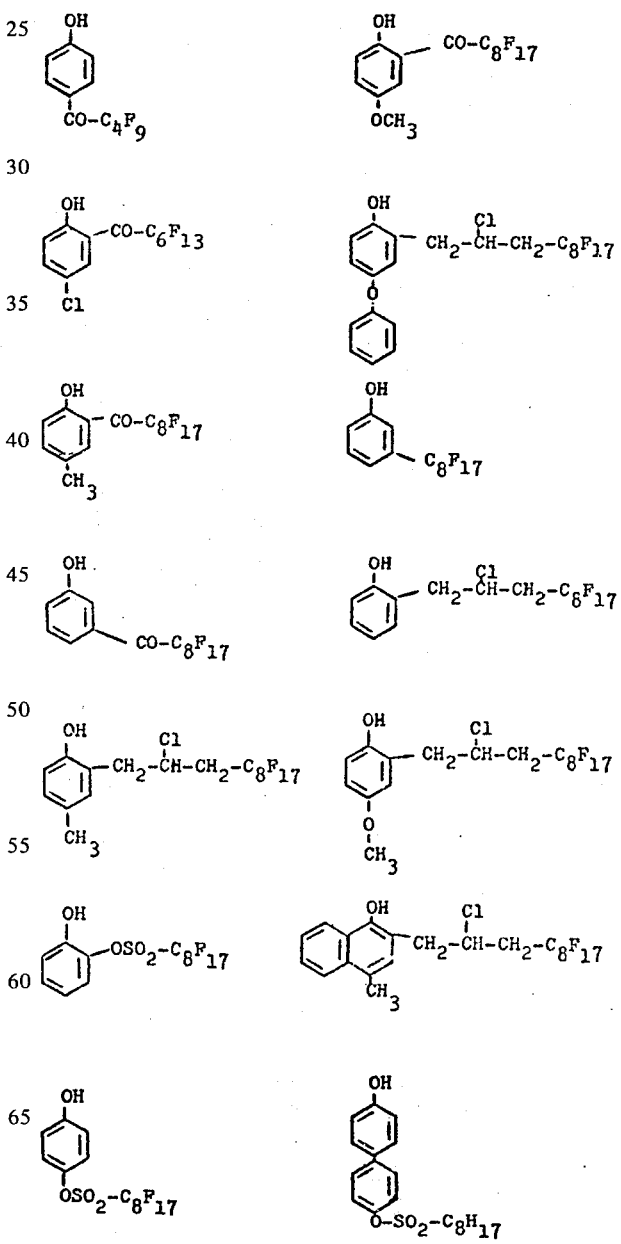

TABLE I continued

[Chemical structures of various fluorinated phenol compounds]

The examples of phenols shown in Table I that may be employed to produce the aldehyde condensation products of this invention are prepared by the reaction of a perfluoroalkyl sulfonyl fluoride, chloride or bromide with a suitable phenol having its hydroxyl(s) protected by acetylation or another method. The preparation of the perfluoroalkyl sulfonyl halides have been described in Brice et al., U.S. Pat. No. 2,732,398. The hydroxy aryl sulfonates shown in Table I may be prepared in accordance with the procedure given in Hansen, U.S. Pat. No. 3,346,612. The carbonyl compounds of Table I may be prepared by Friedel-Crafts reaction of perfluoroalkyl carbonyl chlorides, Ahlbrecht and Husted, U.S. Pat. No. 2,617,817 and phenols in a manner similar to that given in Beilstein, *Organische Che-* mie, Vol. VIII, p. 102 (1925). The perfluoroalkyl sulfonamides may be prepared by the reaction of the perfluoroalkyl sulfonyl chloride or bromide with corresponding aminophenol in accordance with procedures given in Brice and Trott, U.S. Pat. No. 2,732,398.

The phenols of Table I where t is 0 in the general formula of fluoroaliphatic phenols as heretofore described may be prepared according to the process given in Mattson, U.S. Pat. No. 3,326,928.

The pharmaceutical extending medium in the preferred embodiment of the present invention, consists essentially of an aqueous base which may contain thixotropic bodying agents or thickeners. In addition to water, the aqueous base may comprise alcohol or other solvents in amounts up to a few percent, usually not more than about 10 percent by volume. The preferred bodying agent for the oil and water repellent composition of the invention is cetyl alcohol.

The pharmaceutical extending medium consists of all the various ingredients and adjuvants employed as a base except for the formaldehyde condensation product of certain perfluoroalkyl phenols which are added as an alcoholic solution or aqueous dispersion.

Illustrative of the types of materials which can be incorporated optionally in desired amounts for particular purposes are humectants, therapeutic ingredients, perfumes and colorants.

The catalysts which may be used in the present invention are acid or base catalysts. Strong acids, such as sulfonic acids (sulfuric acid) or weak acids such as halogenated aliphatic acids (acetic acid) may be used to prepare novalaks. Preferred acids are trichloroacetic and para-toluene sulfonic acids. Of the many alkaline catalysts which may be used to prepare resoles, sodium hydroxide is preferred. Other catalysts include bases such as the hydroxide oxides and carbonates of lithium, sodium, potassium, cesium, magnesium, calcium, strontium, and barium and zinc oxide. Still other catalysts include ammonia, trimethyl amine, triethyanolamine, and pyridine. The resins obtained from the base catalyzed condensations are called resoles.

As with most phenol aldehyde condensation reactions the character of the product obtained is very dependent on component reactivity, concentration and reaction conditions. It is thus difficult to control the reaction in small scale preparations. In general, the effectiveness of acid catalysts decreases as follows: hydrochloric, nitric, sulfuric, trichloroacetic, oxalic, phosphoric, dichloroacetic, chloroacetic, formic, lactic, and acetic. Also, the more reactive the phenol and aldehyde, the higher the molecular weight and hardness of the novolak obtained.

For the purposes of this invention, desirable condensation products are prepared using mole ratios of fluoroaliphatic phenol to aldehyde of from 1.1:0.3 to 1.0:3.5 or more. The preferred fluoroaliphatic phenol to aldehyde ratios are 1.0:0.6 to 1.0:1.3. Reaction temperatures that may be used are from about 40° C. to about 150° C. or higher and the preferred reaction temperatures are from about 80° C. to about 110° C.

Desirable condensation products that possess oleophobic and hydrophobic properties are obtained when the perfluoroalkyl group of the phenol contains at least 3 carbon atoms up to more than 20 or more carbon atoms. The preferred perfluoroalkyl groups are those containing from about 6 to about 10 carbon atoms.

The lower molecular weight condensation products, in general, are soft waxes having a buttery consistency.

The novolaks prepared from 2-(2'-chloro-3'-perfluorooctyl)-n-propyl phenol and formaldehyde having an average molecular weight of about 800 to about 1500 are soft probably because they are not a precise reaction product but are mixtures of reaction products includng unreacted phenol, phenol reacted with one or more aldehyde molecules, 2 phenol moieties reacted with one or more aldehydes, etc. It is these products that possess the greatest amount of substantivity to skin, leather, wool and polyamide surfaces. The higher molecular weight condensation products; i.e., those with molecular weights over about 1500, are hard, waxy solids and are useful in the preparation of oil and water repellent waxes and polishes. Other uses include coatings and molded products that have water and oil repellency and "easy release" surfaces. Both the lower and higher molecular weight condensation products are useful as a prepolymer to be extended with epoxy groups containing compounds and resins.

The molecular weight range of the soft waxy novolaks will, of course, vary depending upon the nature of the fluoroaliphatic phenol, the aldehyde, the catalyst, the reaction temperature and the like. The use of a strong catalyst reduces the time and temperature required to prepare the product and visa versa.

The method for preparing the novel condensation products of the present invention comprises, generally, the steps of reacting a fluoroaliphatic phenol having the formula

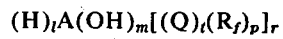

as defined above with an aldehyde having the formula

as defined above in the presence of a condensation catalyst at a temperature of from about 1/2 to 8 hours at a temperature of from about 50° to 150° C.

The present invention will be more clearly understood with reference to the following non-limiting examples wherein all parts are by weight unless otherwise specified.

EXAMPLE 1

Preparation of 2-(2'-chloro-3'-perfluorooctyl)-n-propyl phenol

A 2-liter 3-neck flask equipped with a mechanical stirrer, a sparger tube and means for absorbing sulfur dioxide, and means for heating the flask, was charged with 225.6 grams of 2-allylphenyl acetate (1.45 moles) and heated to 120° C. When the temperature reached 120° C., there was added 0.2 grams of benzoyl peroxide and, over a period of 2 hours, 755 grams (1.45 moles) of perfluorooctane sulfonyl chloride (b.p. 194° C.; $n_D^{25}$ 1.3200) was added while maintaining the temperature at 120° to 140° C. To maintain a concentration of free radicals in the reaction mixture, there was added periodically during the two hours small portions of additional benzoyl peroxide (a total of 1.0 grams including the initial 0.2 grams were added). The mixture was heated at 120° an additional 30 minutes after the addition was complete. Then, without cooling, the flask was rigged for vacuum distillation. Vacuum was applied cautiously to avoid foaming and the mixture distilled. There was obtained 729.2 grams of 2-(2'-chloro-3'-perfluorooctyl-n-propyl) phenyl acetate (79.7 percent conversion) b.p. 140° C./0.40 mm. and unreacted o-allylphenyl acetate. This compound is the precursor for the corresponding phenol.

Into a 10-liter flask equipped with a 2-foot diltillation column and fractionation take-off head and means for heating the flask was placed 729.2 grams (1.16 moles) of 2-(2′-chloro-3′-perfluorooctyl)-n-propyl phenyl acetate, 7 liters of absolute alcohol and 1.0 gram of p-toluene sulfonic acid. The mixture was heated to reflux and over a period of 8 hours after which 4 liters of ethanol were removed by distillation. Of samples taken from the flask during this time, there was an indication of a continued decrease in acetate group contant as determined by infrared analysis. Distillation was continued to remove the remaining ethanol. The residue in the flask was purified by absorption on silica gel and elution with an 80:20 benzene:hexane solution. After removal of the solvent by distillation, taking care not to overheat the product, 637.9 grams of 2-(2′-chloro-3′-perfluorooctyl)-n-propyl phenol was obtained (99.5% of the theoretical amount). Melting point 69°–73° C. Analysis: Calculated for $C_{17}H_{10}ClF_{17}O$; C, 34.7 percent; H, 1.7 percent; 1, 0.7 percent; F, 54.9 percent. Found; C, 34.6 percent; H, O; 1, 1.79 percent; F, 54.8 percent. The above reactions are believed to be properly represented as follows:

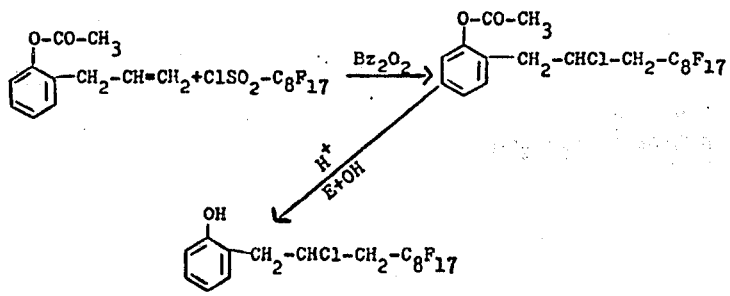

EXAMPLE 2

By performing the procedures of Example 1, using in place of 2-allylphenyl acetate an isomeric mixture of 3- and 5-chloro-2-allyl phenyl acetates, the isomeric mixture of 3- and 5-chloro-2-(2′-chloro-3′-perfluorooctyl)-n-propyl phenyl acetate (b.p. 153° C./0.6 mm.) was prepared from which the isomeric mixture of 3- and 5-chloro-2-(2′-chloro-3′-perfluorooctyl)-n-propyl phenols (yellow wax-like material) may be prepared. Analysis: Calculated for $C_{17}H_9Cl_2F_{17}O$; C, 32.8 percent; H, 1.4 percent; F, 51.8 percent. Found; C, 33.2 percent; H, 1.6 percent; F, 51.8 percent.

EXAMPLE 3

When an isomeric mixture of 3- and 5-methyl-2-allyl phenyl acetates is carried through according to the procedures set out in Example 1 in place of 2-allylphenyl acetate, the isomeric mixture of 3- and 5-methyl-2-(2′-chloro-3′-perfluorooctyl)-n-propyl phenyl acetate was prepared (b.p. 150° C./0.40 mm.) from which the isomeric mixture of 3- and 5-methyl-2-(2′-chloro-3′-perfluorooctyl)-n-propyl phenols (wax-like material) was prepared. Analysis: Calculated for $C_{18}H_{12}ClF_{17}O$; C, 35.8 percent; H, 2.0 percent; F, 53.7 percent; Found; C, 35.8 percent; H, 2.1 percent; F, 53.8 percent.

EXAMPLE 4

Additional -perfluoroalkyl-propyl phenyl acetate and the phenols may be prepared therefrom, are given in Table II.

TABLE II

| ω-Perfluoroalkyl-Propyl Acetate | Corresponding ω-Perfluoroalkyl-Propyl Phenol |
| --- | --- |
| 4-chloro-2-(2′-chloro-3′-perfluorooctyl)-n-propyl phenyl acetate (b.p. 150°C/0.15 mm) | 4-chloro-2-(2′-chloro-3′-perfluorooctyl)-n-propyl phenol (m.p. 88–93° C.) |
| 3,4,6-trichloro-2-(2′-chloro-3′-perfluoro-octyl)-n-propyl phenyl acetate (b.p. 147°C/0.07 mm) | 3,4,6-trichloro-2-(2′-chloro-3′-perfluorooctyl)-n-propyl phenyl (m.p. 84–88° C.) |
| 2,6-dichloro-2-(2′-chloro-3′-perfluorooctyl)-n-propyl phenyl acetate (b.p. 160°C/0.05 mm) | 2,6-dichloro-2-(2′-chloro-3′-perfluorooctyl)-n-propyl phenol (m.p. 88–89° C.) |
| Isomeric mixture of 2,4- and 2,6-diacetoxy-1-(2′-chloro-3′-perfluorooctyl)-n-propyl benzene (b.p. 170°C/0.1 mm) | Isomeric mixture of 2,4- and 2,6-dihydroxy-1-(2′-chloro-3′-perfluorooctyl-n-propyl benzene |

The W-perfluoroalkyl-propyl acetates of Table II were prepared from 4-chloro-2-allyl-phenyl acetate, 3,4,6-trichloro-2-allyl-phenyl acetate, 2,6-dichloro-2-allyl acetate, and an isomeric mixture of 2,4- and 2,6-diacetoxy-allyl-phenyl acetate respectively.

EXAMPLE 5

Table III gives the structure of yet other alkenylphenyl acetates that may be used to prepare additional W-perfluoroalkyl-phenols of this invention. These compounds also may be prepared by following the processes of Example 1 using appropriate properties of W-perfluoro-alkyl sulfonyl halide and alkenyl phenyl acetate.

TABLE III

| Alkenyl Phenyl Acetate | Perfluoroalkyl Sulfonyl Halide | ω-Perfluoroalkyl Alkyl Phenol |
|---|---|---|
| 4-Cl, 2-allyl phenyl acetate | $C_4F_9SO_2Cl$ | 4-Cl, 2-(2-chloro-4,4,5,5,...-$C_4F_9$ alkyl) phenol |
| 4-Cl, 2-allyl phenyl acetate | $C_6F_{13}SO_2Cl$ | 4-Cl, 2-(2-chloro-$C_6F_{13}$ alkyl) phenol |
| 4-Cl, 2-allyl phenyl acetate | $C_8F_{17}SO_2Cl$ | 4-Cl, 2-(2-chloro-$C_8F_{17}$ alkyl) phenol |
| 4-Cl, 2-allyl phenyl acetate | $C_{12}F_{25}SO_2Cl$ | 4-Cl, 2-(2-chloro-$C_{12}F_{25}$ alkyl) phenol |
| 4-Cl, 2-allyl phenyl acetate | $C_{20}F_{41}SO_2Cl$ | 4-Cl, 2-(2-chloro-$C_{20}F_{41}$ alkyl) phenol |
| 4-CH$_3$, 2-allyl phenyl acetate | $C_8F_{17}SO_2Cl$ | 4-CH$_3$, 2-(2-chloro-$C_8F_{17}$ alkyl) phenol |
| 4-phenyl, 2-allyl phenyl acetate | $C_8F_{17}SO_2Cl$ | 4-phenyl, 2-(2-chloro-$C_8F_{17}$ alkyl) phenol |
| 4-Br, 2-allyl phenyl acetate | $C_8F_{17}SO_2Cl$ | 4-Br, 2-(2-chloro-$C_8F_{17}$ alkyl) phenol |

TABLE III-continued
| Alkenyl Phenyl Acetate | Perfluoroalkyl Sulfonyl Halide | ω-Perfluoroalkyl Alkyl Phenol |
|---|---|---|
| 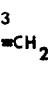 | $C_8F_{17}SO_2Cl$ | 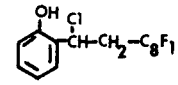 |
|  | $C_8F_{17}SO_2Cl$ | 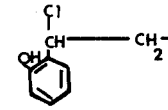 |
|  | $C_{12}H_{25}SO_2Cl$ | 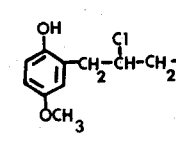 |
|  | $C_{12}F_{25}SO_2Cl$ | 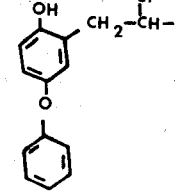 |
| 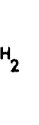 | $C_8F_{17}SO_2Cl$ | 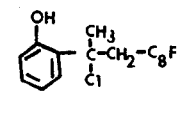 |
| 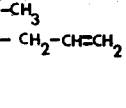 | $C_8F_{17}SO_2Cl$ | 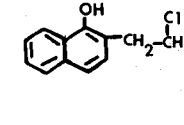 |
| 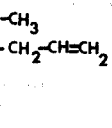 | $C_8F_{17}SO_2Cl$ | 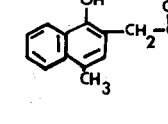 |
| 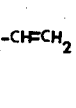 | $C_6F_{13}SO_2Cl$ | 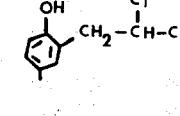 |

TABLE III-continued

| Alkenyl Phenyl Acetate | Perfluoroalkyl Sulfonyl Halide | ω-Perfluoroalkyl Alkyl Phenol |
|---|---|---|
| 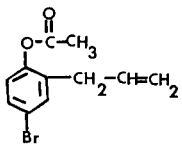 | $C_4F_9SO_2Cl$ | 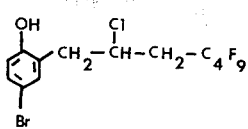 |

The alkenyl-phenyl acetates of Table III and those used in Examples 1 and 2 are prepared from the alkenyl-phenyl ethers which in turn are prepared from the phenols and alkenyl bromides. These reactions are well known procedures. See: J. Am. Chem. Soc., 72, 839–41 (1950): J. Org. Chem. 19, 726–32 (1956); J. Chem. Soc., Japan 57, 599-602 (1956).

For certain applications of the novel phenols of the present invention, it is desirable that there be no chlorine in the alkyl side chain of the ω-perfluoroalkyl chloroalkyl phenol. The chlorine is readily removed by dehydrogenation with a base such as for example, sodium hydroxide, to form a ω-perfluoroalkyl alkenyl phenol and this compound can be hydrogenated to give the corresponding ω-perfluoroalkyl alkyl phenol. Also, ω-perfluoroalkyl alkyl phenols may be prepared by performing the dehydrochlorination and hydrogenation as in Example 6.

EXAMPLE 6

An electrically heated rocking autoclave of 250 ml. capacity was charged with 30 grams of 4-methyl-2-(2'-chloro-3'-perfluorooctyl)-n-propyl phenol (0.05 moles), 8.0 grams of potassium hydroxide, 10 ml. of water, 60 ml. of absolute alcohol and 6.0 grams of Raney nickel catalyst. Hydrogen was introduced at 3,000 p.s.a. pressure and the autoclave was rocked for 4 hours while heating at 150° C. At the end of 4 hours the autoclave was cooled to about 50° C., flushed with nitrogen and opened. The contents were removed and cautiously filtered hot (avoiding spontaneous ignition of the catalyst by keeping it wet at all times), and the catalyst was washed with several 50 ml. portions of hot ethanol. The combined filtrate and washings were stirred into about 250 ml. of water and acidified with dilute hydrochloric acid. The oily layer was separated and purified by absorption on silica gel in a column and elution with a benzene/hexane solvent. After vacuum distillation of the solvent there was obtained about 28 grams of 4-methyl-2-(3'-perfluorooctyl)-n-propyl phenol.

In like manner other ω-perfluoroalkyl-alkyl phenols may be prepared from the corresponding ω-perfluoroalkylchloroalkyl-alkyl phenols, including those given in Table III.

The aldehyde condensation products of this invention may be prepared by the reaction of the perfluoroalkyl phenols disclosed above with aldehydes by well known procedures and in accordance with the following examples.

EXAMPLE 7

Into a 500-ml. 3-neck resin flask equipped with mechanical stirrer, reflux column and thermometer, was placed 100 ml. toluene, 294.3 grams (0.50 moles.) of 2-(2'-chloro-3'-perfluorooctyl)-n-propyl phenol, 15.0 grams (0.50 moles) of paraformaldehyde and 30 grams of trichloroacetic acid. The mixture was stirred and heated at 80° to 85° C. for 3 hours and then at reflux (110° C.) for an additional 2 hours. The solution was cooled to about 50° C., 40 ml. of conc. aqueous ammonia was added, and heat applied to reflux the mixture for an additional hour. The reaction mixture was cooled, washed several times with an equal volume of water, and the solvent removed by vacuum distillation taking care to avoid foaming as the material becomes concentrated.

The condensation product, a novolak, as made in the quantity of this example has a molecular weight by vapor phase osmometry of 1000±100. It is a light yellow soft butterlike wax useful for the preparation of compositions having value in the treatment of skin and render it repellent to oil and water.

EXAMPLE 8

Example 7 was repeated with the exception that 0.05 grams of p-toluenesulfonic acid was used as the condensation catalyst in place of 30 grams of trichloroacetic acid. A novolak was obtained that had a molecular weight by vapor phase osmometry of 1650. It was a tan-colored hard wax.

EXAMPLE 9

Into a 500 ml. 3-neck resin flask equipped with a mechanical stirrer, reflux condenser and thermometer were placed 294.3 grams (0.50 moles) of 2-(2 -chloro, 3'-perfluorooctyl)-n-propyl phenol and 55 grams of formaldehyde (30 percent solution) (0.55 moles). The mixture was stirred and heated to 60° C. and made alkaline to phenolphthalein by dropwise addition of 20 percent sodium hydroxide in water. The mixture was then heated to 90° C. and stirred at this temperature for 4 hours. After this time, the mixture was cooled to 60° C. and acidified (pH: 6.0) with dilute phosphoric acid. The layers were allowed to separate and the yellow viscous lower layer removed from the flask. After drying in vacuum, a waxy yellow resin was obtained. This material is a resol and useful in further condensations to useful polymeric material. It is also useful for the preparation of protective compositions for the treatment of skin and leather.

EXAMPLE 10

Table IV presents the repellency and substantive properties of a number of fluoroaliphatic phenols and condensation products. It may be observed that, in general, monophenols and compounds with more than one OH per carbocyclic ring exhibit only fair oil and detergent repellency on pigskin and are of less substantivity, i.e., little oil and detergent repellency remains after a detergent wash. Fluoroaliphatic phenol aldehyde condensation products having an average molecular weight of about 900 to about 1,600 show good oil and water repellency on pigskin which is very similar to human skin and has the same properties for purposes of testing repellency. They also are substantive to the pigskin as is indicated by the fact that pigskins treated with these condensation products maintain their repellency after a 1-hour wash in a hot detergent solution.

TABLE IV

Properties of Fluoroaliphatic Phenols and Condensation Products

| | Fluoroaliphatic Phenol | Formaldehyde (Condensation Catalyst) | Molecular Weight[b] | Repellency[a] Water | Oil | Substantivity[h] |
|---|---|---|---|---|---|---|
| 1. | 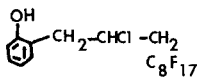 | None[a] | 590 | Fair | None | None |
| 2. | 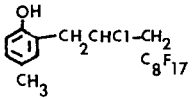 | None[a] | 603 | Fair | None | None |
| 3. | 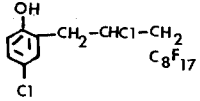 | None[a] | 624 | Fair | None | None |
| 4. | 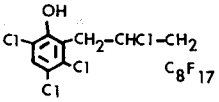 | None[a] | 693 | Fair | None | None |
| 5. | 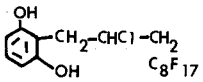 | None[a] | 606 | Fair | Fair | None |
| 6. | 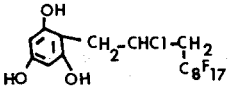 | None[a] | 622 | Fair | Fair | None |
| 7. | 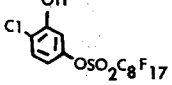 | None[a] | 630 | None | Good | None |
| 8. | 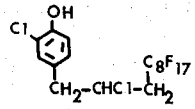 | None[z] | 624 | Fair | None | None |
| 9. | 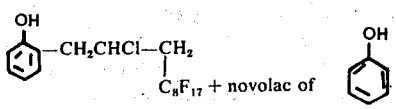 | | 300[f] | Fair | None | None |
| 10. | 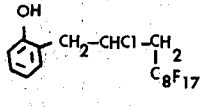 | $CH_2O^c$ | 1100 | Good | Good | Good |
| 11. | 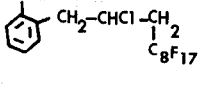 | $CH_2O^d$ | 1650 | Good | Good | Poor |

TABLE IV-continued

Properties of Fluoroaliphatic Phenols and Condensation Products

| | Fluoroaliphatic Phenol | Formaldehyde (Condensation Catalyst) | Molecular Weight[b] | Repellency[a] Water | Oil | Substantivity[h] |
|---|---|---|---|---|---|---|
| 12. | Phenol-CH$_2$-CHCl-CH$_2$-C$_8$F$_{17}$ (OH) | CH$_2$O[d] | 790 | Good | Good | Good |
| 13. | Phenol-CH$_2$-CHCl-CH$_2$-C$_8$F$_{17}$ (OH) | CH$_2$O[c] | 2500 | Good | Good | Poor |
| 14. | Methylphenol-CH$_2$-CHCl-CH$_2$-C$_8$F$_{17}$ (OH, CH$_3$) | CH$_2$O[c] | 980 | Good | Good | Fair |
| 15. | Chlorophenol-OSO$_2$C$_8$F$_{17}$ (OH, Cl) | CH$_2$O[c] | 1150 | Good | Good | Fair |
| 16. | Bis[CH$_2$-CHCl-CH$_2$-C$_8$F$_{17}$]-methylene-bridged dihydroxydimethyl diphenyl | [e] | 1218 | Good | Good | Good |
| 17. | Phenol-CH$_2$-CHCl-CH$_2$-C$_8$F$_{17}$ (OH) | CH$_2$O[d] | >3000 | Fair | Fair | Poor |

[a]Test on the phenol before reaction with aldehyde.
[b]Molecular weight determined by vapor phase osmometry.
[c]Condensation catalyst is trichloroacetic acid.
[d]Condensation catalyst is p-toluenesulfonic acid.
[e]Test on the dihydroxy-diphenyl methane.
[f]Molecular weight of the non-perfluorinated novolac.
[g]After application of an 8% solution to raw pigskin that had been extracted with tetrahydrofurane, dried, and rehydrated to a flexible condition.
[h]Repellency of treated pigskin after it has been given a 1-hour wash with a 0.5% aqueous solution of sodium dodecylbenzene sulfonate at 40° C.

If the perfluorooctyl group of the compounds and products of Table IV are replaced by other perfluoro groups including perfluorobutyl, perfluoroamyl, perfluorohexyl, perfluorododecyl, perfluoroodecyl, and other perfluoroalkyl groups, corresponding compounds and products are obtained that have properties similar to those listed in Table IV.

If the formaldehyde used in the condensation products of Table IV is replaced by other aldehydes including acetaldehyde, benzaldehyde, butyraldehyde, furfuraldehyde, glutaraldehyde, glyoxal, paraldehyde, propionaldehyde, tetrahydrofurfuraldehyde, and other aldehydes desirable condensation products are also obtained that have properties similar to those listed in Table IV.

The following example demonstrates a preferred application of the condensation products of this invention in a composition that provides effective protection of the skin against aqueous and oily material that otherwise might injure the skin.

EXAMPLE 11

To prepare a perfumed protective handcream, an aqueous solution of 82.35 parts of water, 0.3 parts of ammonium lauryl sulfate, and 0.15 parts of Tegosept M (methyl ester of p-hydroxybenzoic acid, a water soluble bactericide) was heated to 50° C. and added to a high shear mixer (Homomixer). An oil phase solution of 3.0 parts of cetyl alcohol, 4.0 parts of the novolak of 2-(2'-chloro-3'-perfluorooctyl)-n-propyl phenol (prepared as described in Example 7), 0.10 parts of Tegosept P (propyl ester of p-hydroxybenzoic acid, an oil soluble bactericide) and 0.004 parts of propyl gallate (antioxidant) was also heated to 50° C. was slowly added to the aqueous mixture, the entire mixture was thoroughly mixed and while mixing, cooled to 32° C., then 0.10 parts of perfume "Flueroma Fragrance No. 9006" available from U.O.P. Fragrances Division of Universal Oil Products, Inc., New York, was added. After the creamy emulsion is cooled to below about 30° C. while mixing, it is discharged from the mixer.

The emulsion was then rubbed onto the hands in the usual manner and was found to be protective against water, oil and detergents.

Handcreams with similar desirable properties may be prepared by using in accordance with Example 11 from 0.5 to 4 parts of cetyl alcohol per 100 parts of handcream. Less cetyl alcohol than 0.5 parts gives thin unstable emulsions and more than 4 parts of cetyl alcohol reduces the oil repellency of the handcream. Likewise, the preferred concentration of perfume or fragrance depends on the type of fragrance used. In general, a useful concentration is from about 0.05 parts up to 0.15 parts per 100 parts of handcream. Less than 0.05 parts of fragrance is ineffective and more than 0.15 may reduce the oil repellency of the handcream. Also, handcreams with desirable properties may be prepared by using in accordance with Example 4 from 0.2 to about 0.4 parts of ammonium lauryl sulfate.

The cream of Example 11 was the result of the study of many formulations to find composites that do not have components that interfere with the substantivity of condensation products of the invention. In general, inorganic thickeners, fugitive surfactants, fluorochemical surfactants, fatty acids, most common surfactants and most fatty alcohols are to be avoided because rather large quantities of these materials are required to achieve emulsion stability. At the high concentration of these materials required the substantivity and repellency of the condensation products of this invention are reduced.

was treated with the test formulation as prepared in Example 11, permitted to dry after which a droplet of soap solution (0.5 percent sodium lauryl sulfonate in deionized water) or oil (75 percent mineral oil of 310 to 320 Saybolt-seconds in heptane) was placed on the surface from a syringe. Pictures taken level with the treated surface at times of 0, 15, 30, 60 and 300 seconds were used to determine the wetting rates of these potential irritants. Initial contact angle as well as rate of change of contact angles were used to compare repellencies of formulations. Substantivity is measured by determining the contact angle of the mineral oil-heptane mixture on the treated callus tissue or pigskin after it is subjected to a 40 minute wash with a 0.5 percent solution of sodium lauryl sulfonate at 45° C., rinsed with warm water and dried.

It may be seen by inspection of Table V that the creams and lotions made using novolaks of 2-2(2'-chloro-3-perfluorooctyl)-n-propyl phenol exhibit oil and soap repellency and that this condensation product is substantive to callus tissue. These results are indicated by the high contact angle of drops of oil on treated callus tissue after it has been washed in hot detergent solution. Creams and lotions made with other novolaks and aldehyde condensation products having an average molecular weight of from about 900 to about 1600 in accordance with the teaching of this invention are repellent to aqueous and oily substances and are substantive to skin and proteinaceous materials.

TABLE V

| | Repellency Tests on Callus Tissue Droplet Contact Angle | | | | | | | |
|---|---|---|---|---|---|---|---|---|
| | Before Detergent Wash | | | | | After Detergent Wash | | |
| Elapsed Time Seconds | Untreated Oil | Untreated Soap | Preparation of Example 11 Oil | Preparation of Example 11 Soap | Preparation of Example 12 Oil | Preparation of Example 12 Soap | Untreated Oil | Preparation of Example 11 Oil | Preparation of Example 12 Oil |
| 2 | 28° | 76° | 89° | 97° | 84° | 101° | <10° | 78° | 75° |
| 15 | 20° | 51° | 82° | 96° | 82° | 99° | Wets | 74° | 72° |
| 30 | 15° | 43° | 80° | 93° | 78° | 96° | out | 70° | 68° |
| 60 | <10° | 27° | 78° | 93° | 76° | 95° | almost | 63° | 64° |
| 300 | <10° | <10° | 76° | 72° | 75° | 84° | immediately | 47° | 52° |

EXAMPLE 12

A protective lotion was prepared by dissolving 0.004 parts of propyl gallate, 4 parts of the novolak of 2-(2'-chloro-3'-perfluorooctyl)-n-propyl phenol (prepared as in Example 1) and 0.1 part of perfume in 96 parts of denatured ethyl alcohol. The resulting lotion provided protection of the hands against hot soapy water. When applied to the hands and other parts of the body, the cream provided protection against aqueous and oily solutions. In place of denatured ethyl alcohol, isopropanol or a Freon or a mixture of one or mre Freons having a boiling point of about 70° F. to about 150° F. may be used. If the lotion is to be used to treat leather, textiles, or synthetic materials, then other solvents may be used including diethyl ether, acetone, methyl ethyl ketone, amyl acetate, benzene, chlorinated hydrocarbons and the like.

EXAMPLE 13

The repellency and substantive properties of the protective compositions of this invention were determined by photographically measuring droplet contact angles over a five minute period. Pigskin or callus tissue

EXAMPLE 14

An aerosol spray embodying the composition of the invention is prepared by charging a 6 ounce aerosol can with 90 grams of a 4 percent solution of the novolak of 2-(2'-chloro-3'-perfluorooctyl)-n-propyl phenol (prepared as in Example 7) in ethanol and 90 grams of a 40:60 mixture of Freon 11 and Freon 12. To disperse the protective composition, the aerosol can is equipped with a "Precision" valve and dip tube. When sprayed on the hands or other parts of the body, a pleasant emollient character is noted and the hands and body are afforded protection against oil and aqueous based irritants, acid and basic solutions even after the hands and body are washed in water or detergent solutions.

What is claimed is:

1. A condensation polymer having an average molecular weight of about 800 to about 1500 of the condensation catalyst catalyzed reaction of a phenol of the formula

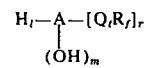

wherein $l$, $m$ and $r$ are 1 or 2, $t$ is 1; H is a hydrogen atom sufficiently reactive to undergo a catalyzed condensation reaction with an aldehyde; A is an aryl nucleus containing from 6 to 15 carbon atoms; OH is a phenolic hydroxyl group; $R_f$ is a monovalent fluorinated saturated aliphatic radical containing from 3 to 20 carbon atoms and Q is selected from the class consisting of carbonyl and carbonamide and a saturated aliphatic aldehyde containing not more than 7 carbon atoms in addition to the aldehyde carbon atom or benzaldehyde.

2. A condensation polymer having an average molecular weight of about 900 to about 2500 of the condensation catalyst catalyzed reaction of a phenol of the formula

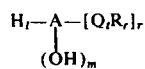

wherein $l$, $m$ and $r$ are 1 or 2, $t$ is 1; H is a hydrogen atom sufficiently reactive to undergo a catalyzed condensation reaction with an aldehyde; A is an aryl nucleus containing from 6 to 15 carbon atoms; OH is a phenolic hydroxyl group; $R_f$ is a monovalent fluorinated saturated aliphatic radical containing from 3 to 20 carbon atoms and Q is selected from the class consisting of carbonyl and carbonamide and a saturated aliphatic aldehyde containing not more than 7 carbon atoms in addition to the aldehyde carbon atom or benzaldehyde.

3. A polymer according to claim 1 wherein the aldehyde is formaldehyde.

4. A polymer according to claim 3 wherein the phenol is

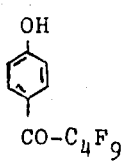

* * * * *